United States Patent
Córdova et al.

(10) Patent No.: US 11,168,050 B2
(45) Date of Patent: *Nov. 9, 2021

(54) EFFICIENT SYNTHESIS OF AMINES AND AMIDES FROM ALCOHOLS AND ALDEHYDES BY USING CASCADE CATALYSIS

(71) Applicant: XP Chemistries AB, Stockholm (SE)

(72) Inventors: Armando Córdova, Stockholm (SE); Per Berglund, Stockholm (SE); Mattias Anderson, Stockholm (SE); Samson Afewerki, Uppsala (SE)

(73) Assignee: XP Chemistries AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/129,424

(22) PCT Filed: Mar. 27, 2015

(86) PCT No.: PCT/EP2015/056776
§ 371 (c)(1),
(2) Date: Sep. 27, 2016

(87) PCT Pub. No.: WO2015/144902
PCT Pub. Date: Oct. 1, 2015

(65) Prior Publication Data
US 2017/0174618 A1 Jun. 22, 2017

Related U.S. Application Data

(60) Provisional application No. 61/971,106, filed on Mar. 27, 2014.

(51) Int. Cl.
| | | |
|---|---|---|
| *C12P 13/00* | (2006.01) | |
| *C12P 13/02* | (2006.01) | |
| *C07C 233/27* | (2006.01) | |
| *C07C 231/02* | (2006.01) | |
| *C07C 231/10* | (2006.01) | |
| *C07C 233/25* | (2006.01) | |
| *C12N 9/02* | (2006.01) | |
| *C12N 9/10* | (2006.01) | |

(52) U.S. Cl.
CPC .......... *C07C 233/27* (2013.01); *C07C 231/02* (2013.01); *C07C 231/10* (2013.01); *C07C 233/25* (2013.01); *C12P 13/001* (2013.01); *C12P 13/02* (2013.01)

(58) Field of Classification Search
CPC .. A61K 2300/00; A61K 31/52; C07C 233/25; C07C 233/27; C12P 13/001; C12P 13/02
USPC .......... 435/176, 184, 129; 424/94.1
See application file for complete search history.

(56) References Cited

FOREIGN PATENT DOCUMENTS

| WO | WO-2006/038049 A1 | 4/2006 | |
|---|---|---|---|
| WO | WO2012/0287 | * | 3/2012 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Shin et al. JACS. 2002, pp. 2848-2853.*
Garade et al. Appld clay sci 2011, 53, pp. 157-163).*
Chowdhury et al. ( Ind Eng Chem Res. 2009, 48, 9471-9478.*
Nelson et al. JACS, 1919, 41, pp. 2121-2130.*
Kobata et al. (Biotech 1998, 20, pp. 451-454.*
Gannet et al. J. Org. Chem. 1988, 53, p. 1064-1071.*
Samridhi Lal. PhD thesis Apr. 2014, University of central lanshire UK.*
Montallbetti Etal. Tetrahedron report 2005, 61, pp. 10827-10852.*
Zhu et al. J. Phy. Chem.2011,pp. 24743-24749.*
A Lerchner et al., "Coupled Enzymatic Alcohol-to-Amine Conversion of Isosorbide using Engineered Transaminases and Dehydrogenases", vol. 5, Issue 11, CHEMCATCHEM, pp. 3374-3383, Aug. 16, 2013.
C. Palo-Nieto et al., "Integrated Heterogeneous Metal/Enzymatic Multiple Relay Catalysis for Eco-Friendly and Asymmetric Synthesis", vol. 6, ACS CATAL., pp. 3932-3940, May 16, 2016.
J. H. Sattler, et al., "Redox Self-Sufficient Biocatalyst Network for the Amination of Primary Alcohols", vol. 51, Issue 36, Angew. Chem., Int. Ed., pp. 9156-9159, Sep. 3, 2012.
K. Tauber et al., "Artificial Multi-Enzyme Networks for the Asymmetric Amination of sec-Alcohols", vol. 19, Issue 12, CHEM.—EUR.J., pp. 4030-4035, Jan. 22, 2013.
M. Anderson et al., "Total Synthesis of Capsaicin Analogues from Lignin-Derived Compounds by Combined Heterogeneous Metal, Organocatalytic and Enzymatic Cascades in One Pot", vol. 356, Issue 9, Adv. Synth. Catal., pp. 2113-2118, Jun. 16, 2014.

(Continued)

*Primary Examiner* — Robert B Mondesi
*Assistant Examiner* — Mohammad Y Meah
(74) *Attorney, Agent, or Firm* — Welsh IP Law LLC

(57) ABSTRACT

The present invention relates generally to an eco-friendly methodology for the conversion of alcohols and aldehydes to amines and amides using an integrated enzyme cascade system with metal- and organocatalysis. More specifically, the present invention relates to synthesis of capsaicinoids starting from vanillin alcohol and using a combination of an enzyme cascade system and catalysts. Furthermore, the method also relates to synthesis of capsaicinoids derivatives starting from vanillin alcohol derivatives and using a combination of an enzyme cascade system and catalysts.

35 Claims, No Drawings

(56) References Cited

OTHER PUBLICATIONS

M. Fuchs et al., "Amination of Benzylic and Cinnamic Alcohols via a Biocatalytic, Aerobic, Oxidation-Transamination Cascade", vol. 2, RSC ADV., pp. 6262-6265, Jun. 12, 2012.
M. Pickl et al., "Amination of ?-Functional Aliphatic Primary Alcohols by a Biocatalytic Oxidation-Transamination Cascade", vol. 7, Issue 19, CHEMCATCHEM, pp. 3121-3124, Oct. 5, 2015.
Chinese Office Action and Translation Application No. 201580022979.5 dated Dec. 4, 2017 23 pages.
Chinese Office Action w/ translation Application No. 201580022979.5 dated Sep. 6, 2018 22 pages.
Vasant R. Choudhary, et al. "Oxidation of Benzyl Alcohol to Benzaldehyde by tert-Butyl Hydroperoxide over Nanogold Supported on TiO2 and other Transition and Rare-Earth Metal Oxides", Industrial & Engineering Chemistry Research, Nov. 2009 48 (21), pp. 9471-9478.
Office Action from Canada Application No. 2,943,677 dated Sep. 19, 2018.
Peter M. Gannett et al., "The Capsaicinoids: Their Separation, Synthesis, and Mutagenicity," The Journal of Organic Chemistry, American Chemical Society, Jan. 1, 1988, pp. 1064-1071, vol. 53, No. 5.
Kenji Kobata et al., "Enzymatic Synthesis of Capsaicin Analogs with Liver Acetone Powder," *Tetrahedron Letters*, Apr. 15, 1996, pp. 2789-2790, vol. 37, No. 16.

\* cited by examiner

EFFICIENT SYNTHESIS OF AMINES AND AMIDES FROM ALCOHOLS AND ALDEHYDES BY USING CASCADE CATALYSIS

CROSS-REFERENCE TO PRIOR APPLICATIONS

This application is a § 371 National Stage Application of PCT International Application No. PCT/EP2015/056776 filed Mar. 27, 2015, which claims priority to U.S. Provisional Application No. 61/971,106 filed Mar. 27, 2014, each of which are herein incorporated by reference in their entirety.

FIELD OF INVENTION

The present invention relates generally to eco-friendly methodology for the conversion of alcohols and aldehydes to amines and amides using an integrated enzyme cascade system with metal- and organocatalysis. More specifically, the present invention relates to synthesis of capsaicinoids starting from vanillin alcohol and using a combination of an enzyme cascade system and catalysts.

BACKGROUND

Amines and amides are useful and highly valuable compounds for the production of fine chemicals and pharmaceuticals. In this context, Capsaicin (7a) is a pungent compound found in *Capsicum* spp, and is responsible for the hot and spicy taste of the red pepper fruits of these plants.[1] Several capsaicin analogues 7 (or capsaicinoids) can also be found in *Capsicum* spp, but capsaicin is one of the most commonly occurring and also the first one to be isolated and have its structure determined.[1-4] Applications of capsaicinoids include spicy foods, self-defense weapons (such as pepper spray) and analgesics such as Zostrix and Axsain. Capsaicinoids have also been shown to have a variety of other physiological effects, for example activation of both heat loss and heat productions, increase of adrenal catecholamine secretion[6,7] and suppression of body fat accumulation[7,8]. Capsaicinoids also show cancer-suppressing properties (see 9-11 for reviews on the subject).

Capsaicinoids (7) can be isolated from natural sources (e.g. *Capsicum* spp pepper fruits), but this gives predominantly capsaicin (7a) and dihydrocapsaicin since many of the other capsaicinoids are present only in trace amounts.[3,4] Chemical synthesis is thus useful to obtain the more uncommon capsaicinoids such as nonivamide (7b), and for making non-natural capsaicinoids.[12] Capsaicinoids can be prepared from vanillin (2) by first reducing vanillin oxime using a mixture of an excess of metal (Zn) and ammonium formate in MeOH under reflux to obtain vanillylamine (4).[13] Next, 4 can be further reacted with acyl chlorides (6) to form the final products (7).[12,14-16] Alternatively, the amide bond-formation can be accomplished by an enzyme-catalysed transformation between 4 and different fatty acid derivatives.[17-20]

Lignin derived from wood is a natural source for the production of vanillyl alcohol (1) and vanillin (2),[21] and it is therefore a possible raw material for the synthesis of capsaicinoids (7). Lignin is especially interesting since it is renewable, available in large quantities in Nature and currently only used for a limited number of applications.[21,22] Vanillin can also be synthesized from guaiacol by reacting it with glyoxylic acid by electrophilic aromatic substitution. The resulting vanillylmandelic acid is next converted via 4-Hydroxy-3-methoxyphenylglyoxylic acid to vanillin (2) by oxidative decarboxylation.[23]

However there is a need for an environmentally benign method for the manufacture of capsaicinoids. More specifically, there is a need of an enzymatic approach to prepare the intermediate amine, such as vanillylamine (4a), in order to eliminate the need to use metal for the reductive amination step, i.e. the step of converting an aldehyde to its corresponding amine as in the conversion of vanillin to vanillylamine. Furthermore, there is a need for more efficient methods of converting vanillylamine and its derivatives to capsaicinoids wherein the yields of said capsaicinoids are higher than the yields described in prior art. Moreover, there is also a need of manufacturing capsaicinoids in one pot without the need of purifying reaction intermediates.

OBJECT OF THE INVENTION

It is an object of the invention to use various renewable compounds as starting materials for the synthesis of amines and amides.

A further object of the invention is to provide a method of synthesis of amines and amides that is advantageous from an environmental and health standpoint.

A further object of the invention is to provide a more sustainable process for the manufacture of amides.

A further object of the invention is to perform the synthesis in one pot.

A further object of the invention is to eliminate the need for isolation of intermediates.

A further object of the invention is to reduce the amount of waste formed in the synthesis.

A further object of the invention is to use an enzymatic approach to prepare the intermediate vanillylamine (4a) in order to eliminate the need to use metal for the reductive amination step.

SUMMARY OF INVENTION

The objects of the invention are attained by using a multi-catalytic cascade relay sequence involving an enzyme cascade system that when integrated with other catalytic systems, such as heterogeneous metal catalysts and organic catalysts, converts an alcohol to an amine and amide in sequence or in one-pot, respectively. Embodiments of the present invention are illustrated in Scheme 1, wherein (i) R is preferably selected from aliphatic, aryl, 4-hydroxy-3-methoxy-$C_6H_3$, and 4-hydroxy-3-ethoxy-$C_6H_3$, (ii) $R^1$ is preferably is selected from H, methyl and ethyl, and (iii) $R^3$ is preferably selected from alky and aryl.

As indicated in Scheme 1, embodiments relate to a method for conversion of an alcohol comprising the steps of (a) converting said alcohol to an aldehyde or a ketone, (b) converting said aldehyde or ketone to an amine, wherein the conversion of said aldehyde or ketone to amine is catalyzed by an enzyme cascade system, and (c) converting said amine to said amide.

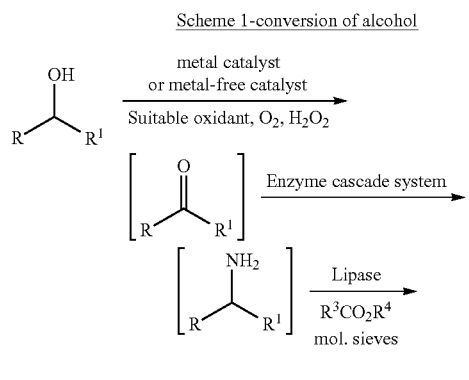

Further embodiments relate to the synthesis of capsaicinoids and similar derivatives by the conversion of vanillyl alcohol and its derivatives using a combination of multi-catalysis systems as illustrated in Scheme 2.

Further embodiments relate to the synthesis of capsaicinoids and similar derivatives starting from vanillin and its derivatives using an enzyme cascade system and an organocatalyst as illustrated in Scheme 2.

Further embodiments relate to the synthesis of capsaicin, nonivamide and phenylcapsaicin, as well as derivatives thereof.

Further embodiments relate to a method for conversion of an alcohol comprising the steps of (a) converting said alcohol to an aldehyde, (b) converting said aldehyde an amine, wherein the conversion of said aldehyde to amine is catalyzed by an enzyme cascade system, and (c) converting said amine to said amide, wherein steps said steps a-c are conducted by using alcohols, aldehydes, amines and reagents disclosed in Scheme 3.

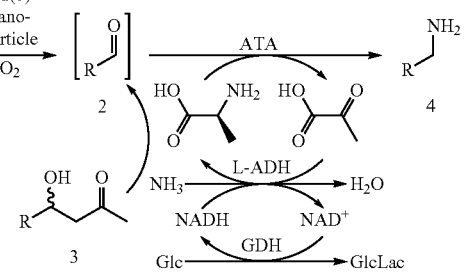

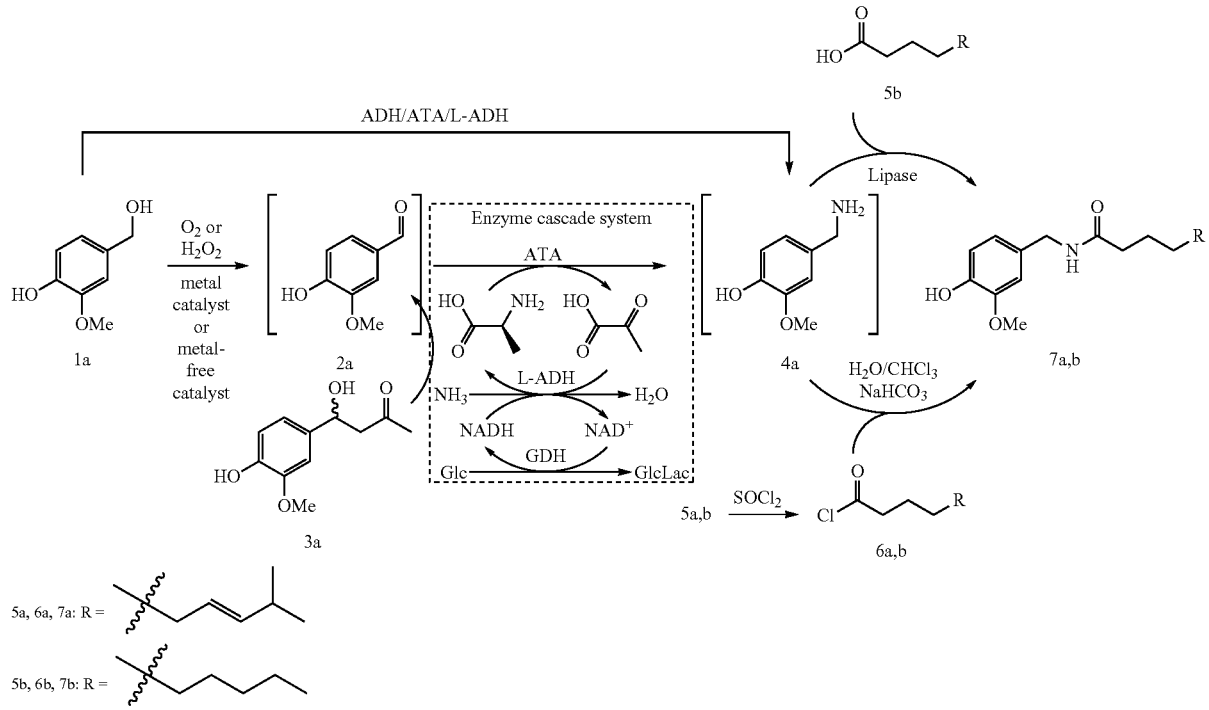

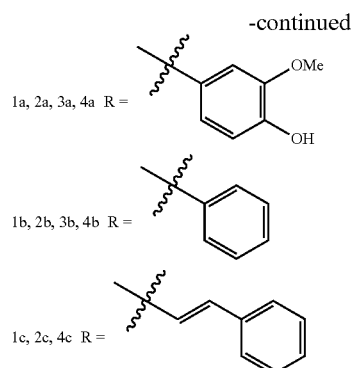

Further embodiments relate to the conversion of alcohols to amines and amides under environmentally benign conditions.

Thus, in different embodiment aspects the objects are achieved by:

Synthesizing amines and amides from alcohols using multi-catalytic cascade relay sequences.

Synthesizing amines and amides from aldehydes using multi-catalytic cascade relay sequences.

Performing the total synthesis of capsaicinoids starting from vanillin and its derivatives using multi-catalytic cascade relay sequences.

Performing the total synthesis of capsaicinoids starting from vanillyl alcohol and its derivatives using multi-catalytic cascade relay sequences.

DETAILED DESCRIPTION

The described embodiments relate to an environmentally benign method for conversion of an alcohol wherein the method comprises the steps of converting an alcohol to an aldehyde or ketone, converting the aldehyde or ketone to an amine, and then converting the amine to an amide. The conversion of the aldehyde to an amine is catalyzed by an enzyme cascade system.

An alcohol which is used for preparing the aldehyde may be selected from a primary alcohol. The oxidation of the primary alcohol results in an aldehyde which comprises an R group where R is chosen from alkyl, aryl, cinnamyl and heterocyclic. The conversion of the aldehyde to an amine by the enzyme cascade system results in an amine comprising an R group where R is chosen from alkyl, aryl, cinnamyl and heterocyclic. The amine which is subjected to an acylating agent yields an amide having an R group wherein R is chosen from alkyl, aryl, cinnamyl and heterocyclic, as well as an acyl group ($COR^3$) wherein $R^3$ is chosen from alkyl and aryl.

A secondary alcohol may be used for preparing the ketone. The oxidation of the secondary alcohol results in a ketone keto-group comprising an R group wherein R is chosen from alkyl and aryl, as well as an $R^1$ group wherein $R^1$ is chosen from methyl and ethyl. The conversion of the ketone to an amine by the enzyme cascade system results in an amine comprising an R group wherein R is chosen from alkyl and aryl, as well as, an $R^1$ group wherein $R^1$ is chosen from methyl and ethyl. The amine which is subjected to an acylating agent yields an amide having (i) an R group wherein R is chosen from alkyl and aryl, (ii) an $R^1$ group wherein $R^1$ is chosen from methyl and ethyl, and (iii) acyl ($COR^3$) wherein $R^3$ is chosen from alkyl and aryl.

The alcohol is converted to the aldehyde by a suitable catalyst depending on the nature of the reactive molecule. The catalyst is selected from a heterogeneous (supported) metal catalyst, homogeneous metal catalyst (such as homogeneous organometallic complex), a metal-free catalyst (mediator) or an oxidizing enzyme (such as oxidizing enzyme EC 1:10:3:2). A suitable oxidant, depending on the nature of the reactive molecule, is selected from oxygen, air, hydrogen peroxide and NaOCl.

An alcohol which is used for preparing the aldehyde may be selected from an aldol. The degradation of the aldol results in an aldehyde which comprises an R group where R is chosen from alkyl, aryl, cinnamyl and heterocyclic. The conversion of the aldehyde to an amine by the enzyme cascade system results in an amine comprising an R group where R is chosen from alkyl, aryl, cinnamyl and heterocyclic. The amine which is subjected to an acylating agent yields an amide having an R group wherein R is chosen from alkyl, aryl, cinnamyl and heterocyclic, as well as an acyl group ($COR^3$) wherein $R^3$ is chosen from alkyl and aryl.

The enzyme cascade system which converts the aldehyde to its corresponding amine comprises Amine Transaminase (ATA) which may be combined with an organic catalyst such as an amine donor selected from alanine, IPA (isopropylamine) and methylbenzyl amine. The preferred amine donor is L-alanine and preferred ATA is EC 2.6.1.18. Interestingly, the inclusion of $NH_3$ (for example in the form as ammonium chloride) as terminal N-source, L-alanine dehydrogenase and NADH in the enzyme cascade system increases the yield of the amide. Moreover, the yield of the amide may be further increased by also including of D-Glucose and glucose dehydrogenase in the enzyme cascade system. Hence, an optimal conversion involves the use of an enzyme cascade system comprising ATA, L-alanine, $NH_3$, L-alanine dehydrogenase, NADH, D-Glucose, glucose dehydrogenase.

The conversion of the amine to its corresponding amide is achieved by acylating the amine with an acylating agent (i.e. amidation agent) selected from acids, alkyl ketene dimers, acid chlorides and anhydrides. Moreover, catalytic methods involving for example organocatalysts and lipases may also be used.

The above described method for the manufacture of an amide may be used for the manufacture of capsaicinoids and its derivatives as indicated in Scheme 2 (shown above) which illustrates the use of a multi-catalytic cascade relay sequence (i.e. a multi-catalysis system).

As illustrated, vanillin (2a) is be prepared either from vanillyl alcohol (1a) or the aldol of formula 3. In the next step vanillin is converted to its corresponding amine vanillylamine (4a) by the enzyme cascade system. The capsaicinoids of formula 7a and 7b may be prepared by two different routes. The first route involves the reaction of vanillylamine with compound of formula 5a or 5b while the second route instead involves the reaction of vanillylamine with compound of formula 6a or 6b. In further preferred embodiments, derivatives of 1a, 2a and/or 3a, may be used for manufacturing phenylcapsaicin as well as natural and non-natural capsaicinoids.

In preferred embodiments the acylating gents 5a, 5b, 6a and 6d may be replaced by 7-phenylhept-6-yonic acid and compounds of formula

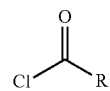

wherein the R group is selected from (i) alkyl, (ii) aryl and (iii) heterocyclic.

The preferred embodiments of the present invention utilize a renewable compound such as lignin as a source of vanillyl alcohol. Moreover, the preferred embodiments of the invention is performed in one pot without any purification of intermediates. The use of renewable compounds, an enzyme cascade system without metals catalysis and one pot synthesis renders the present invention sustainable and environmentally benign.

In preferred embodiments of the invention, benzyl alcohols, cinnamyl alcohols, and hydroxyl-, methoxy- and ethoxybenzyl alcohols may be used as starting compounds. Specific embodiments involve the use of alcohols with formula RCHOHR1 wherein R is selected from aliphatic, aryl, 4-hydroxy-3-methoxy-$C_6H_3$, and 4-hydroxy-3-ethoxy-$C_6H_3$, and wherein $R_1$ is selected from H, methyl and ethyl. Moreover, preferred embodiments may involve the use of aldehydes and ketones as starting compounds wherein benzaldehydes and arylmethyl ketones are some examples. The starting alcohols, aldehydes and ketones may have been obtained from petroleum based or renewable resources.

Alkyl is in the present invention a straight or branched carbon chain of between 1 and 30 carbon atoms (C1-30) in length, wherein said carbon chain may be optionally unsaturated, thus including alkenes and alkynes. Said C1-30 alkyl group may be optionally substituted with from 1-3 substituents, wherein said substituents are selected from alkoxy (C1-30 straight or branched), halogen, hydroxyl, nitro, cyano, and phenyl (wherein said phenyl is optionally substituted with from 1-3 substituents selected independently from the group consisting of alkyl, alkoxy (C1-30 straight or branched), halogen, hydroxyl, cyano and nitro).

Aryl is in the present invention an aromatic group which may be optionally substituted with from 1-3 substituents, wherein said substituents are selected from alkyl, alkoxy (C1-30 straight or branched), halogen, hydroxyl, nitro, cyano, and phenyl (wherein said phenyl is optionally substituted with from 1-3 substituents selected independently from the group consisting of alkyl, (C1-30 straight or branched), halogen, hydroxyl, cyano and nitro).

Cinnamyl is in the present invention a cinnamyl group which may be optionally substituted with from 1-3 substituents, wherein said substituents are selected from alkyl, alkoxy (C1-30 straight or branched), halogen, hydroxyl, nitro, cyano, and phenyl (wherein said phenyl is optionally substituted with from 1-3 substituents selected independently from the group consisting of alkyl, halogen, hydroxyl, cyano and nitro).

Heterocyclic is in the present invention a heterocyclic group which may be optionally substituted with from 1-3 substituents, wherein said substituents are selected from alkyl, alkoxy (C1-30 straight or branched), halogen, hydroxyl, nitro, cyano, and phenyl (wherein said phenyl is optionally substituted with from 1-3 substituents selected independently from the group consisting of alkyl, alkoxy (C1-30 straight or branched), halogen, hydroxyl, cyano and nitro).

EXPERIMENTAL SECTION

Chemicals and solvents were either purchased puriss p. A. from commercial suppliers or were purified by standard techniques. Commercial reagents were used as purchased without any further purification.

*Chromobacterium violaceum* amine transaminase (ATA) was produced by fermentation. L-alanine dehydrogenase (L-ADH, from *Bacillus cereus*, ≥350 U/mL, product number 79848) and glucose dehydrogenase (GDH, from *Pseudomonas* sp., ≥200 U/mg, product number 19359) were purchased from Sigma-Aldrich.

Aluminum sheet silica gel plates (Fluka 60 F254) were used for thin-layer chromatography (TLC), and the compounds were visualized by irradiation with UV light (254 nm) or by treatment with a solution of phosphomolybdic acid (25 g), $Ce(SO_4)_2.H_2O$ (10 g), conc. $H_2SO_4$ (60 mL), and $H_2O$ (940 mL), followed by heating. Purification of the product was carried out by flash column chromatography using silica gel (Fluka 60, particle size 0.040-0.063 mm).

HPLC analysis was performed with a 1100 series HPLC system (Agilent) using a Crownpak CR(+) column (Daicel) and a UV detector (254 nm). An acidic mobile phase with pH 1.6 ($HClO_4$) and 10% v/v methanol was used. Conversions were determined by measuring the formed product and comparing it to a standard curve, using benzoic acid as internal standard.

Infrared (IR) spectra were recorded on Thermo Fisher Nicolet 6700 FT-IR spectrometer, λmax in $cm^{-1}$. Bands are characterized as broad (br), strong (s), medium (m), or weak (w). NMR spectra were recorded on a Bruker Avance (500 MHz or 400 MHz) spectrometer. Chemical shifts are reported in ppm from tetramethylsilane with the solvent resonance resulting from incomplete deuterium incorporation as the internal standard ($CDCl_3$: δ 7.26 ppm). Data are reported as follows: chemical shift, multiplicity (s=singlet, d=doublet, q=quartet, br=broad, m=multiplet), and coupling constants (Hz), integration. $^{13}C$ NMR spectra were recorded on a Bruker Avance (125.8 MHz or 100 MHz) spectrometer with complete proton decoupling, Chemical shifts are reported in ppm from tetramethylsilane with the solvent resonance as the internal standard ($CDCl_3$: δ 77.16 ppm). High-resolution mass spectrometry was performed on Agilent 6520 Accurate-Mass Q-TOF LC/MS (positive mode).

ATA: Cloning, Expression and Purification

The gene for the *Chromobacterium violaceum* amine transaminase (ATA) was inserted into plasmid pET28a(+) and transformed into *Escherichia coli* BL21 (DE3) cells as described previously by Cassimjee et. al.[24] Cells containing the transaminase plasmid were cultivated overnight in 20 mL Luria-Bertoni (LB) medium (10 g/L tryptone, 5 g/L NaCl, 5 g/L yeast extract) with 50 mg/L kanamycin in 37° C. and 220 rpm. Protein expression was performed by mixing six of these overnight cultures with 1080 mL LB medium and 50 mg/L kanamycin in a baffled flask, in 25° C. and 120 rpm. The culture was induced by addition of 0.4 mM IPTG and incubated for 24 h. The cells were then harvested and separated from the medium by centrifugation. The cells were resuspended in IMAC binding buffer consisting of 20 mM $Na_2HPO_4$ and 500 mM NaCl, pH 7.4, and disrupted by sonication. Cell debris was removed by centrifugation and the crude enzyme solution was filtered (0.45 μm) and purified with an AKTA FPLC system using a HisTrap HP 5 mL column (GE Healthcare). Binding buffer was used to wash the column, and the enzyme was then eluted with an IMAC elution buffer consisting of 20 mM $Na_2HPO_4$, 500 mM imidazole and 500 mM NaCl, pH 7.4. The enzyme solution was incubated with 1 mM pyridoxal-5'-phosphate (PLP) for 20 minutes with gentle mixing. The buffer was then changed to HEPES 50 mM pH 8.2 using a PD10 desalting column (GE Healthcare). The enzyme was stored overnight before being used for reactions. The enzyme was stored in darkness and 4° C Determination of ATA Concentration ATA concentration was determined by measuring the absorbance at 395 nm, with an extinction coefficient of 8.1 mM$^{-1}$cm$^{-1}$, as described by Cassimjee et. al.[24]

Preparation of Vanillylamine from Vanillin

All reactions were performed at 37° C. and darkness in eppendorf tubes mL total volume). Conversions were determined by HPLC analysis.

In the first experiments, 250 mM L-alanine and 5 mM vanillin (2a) were mixed in HEPES buffer 50 mM pH 8.2, together with 0.2 mg/mL ATA. After 23 h, 25% of the vanillin had been converted into vanillylamine (4a). The same experiment was repeated with the addition of the L-alanine dehydrogenase. Since no NADH regeneration system was used for this experiment, an excess (2 eq) of NADH was used. The reaction composition was 250 mM L-alanine, 5 mM vanillin, too mM ammonium chloride and to mM NADH in HEPES buffer 50 mM pH 8.2, together with 0.2 mg/mL ATA and 7 U/mL L-alanine dehydrogenase. This resulted in a conversion of 70% after 23 h. The experiment was then repeated with the addition of glucose dehydrogenase to regenerate NADH. With the presence of the regeneration system, NADH concentration in the reaction was changed from excess to a catalytic amount. The reaction composition was 250 mM L-alanine, 5 mM vanillin, too mM ammonium chloride, too mM D-glucose and 1 mM NADH in HEPES buffer 50 mM pH 8.2, together with 0.2 mg/mL ATA, 7 U/mL L-alanine dehydrogenase and to U/mL glucose dehydrogenase. In 23 h, this system resulted in a conversion of >99%.

The starting concentration of vanillin (2a) in the reaction could successfully be increased to 50 mM while maintaining a high conversion. Vanillin was first dissolved in DMSO and then mixed with D-glucose, ammonium chloride and L-alanine in HEPES buffer 50 mM. The pH was adjusted to 8.2 (1 M NaOH) and the solution was mixed with NADH and the enzymes in an eppendorf tube to give the final concentrations 250 mM L-alanine, 50 mM vanillin, 150 mM ammonium chloride, 150 mM D-glucose, 1 mM NADH and to % DMSO v/v, together with 0.9 mg/mL ATA, 7 U/mL L-alanine dehydrogenase and to U/mL glucose dehydrogenase. This resulted in a conversion of 95% after 17 h.

Preparation of Other Amines

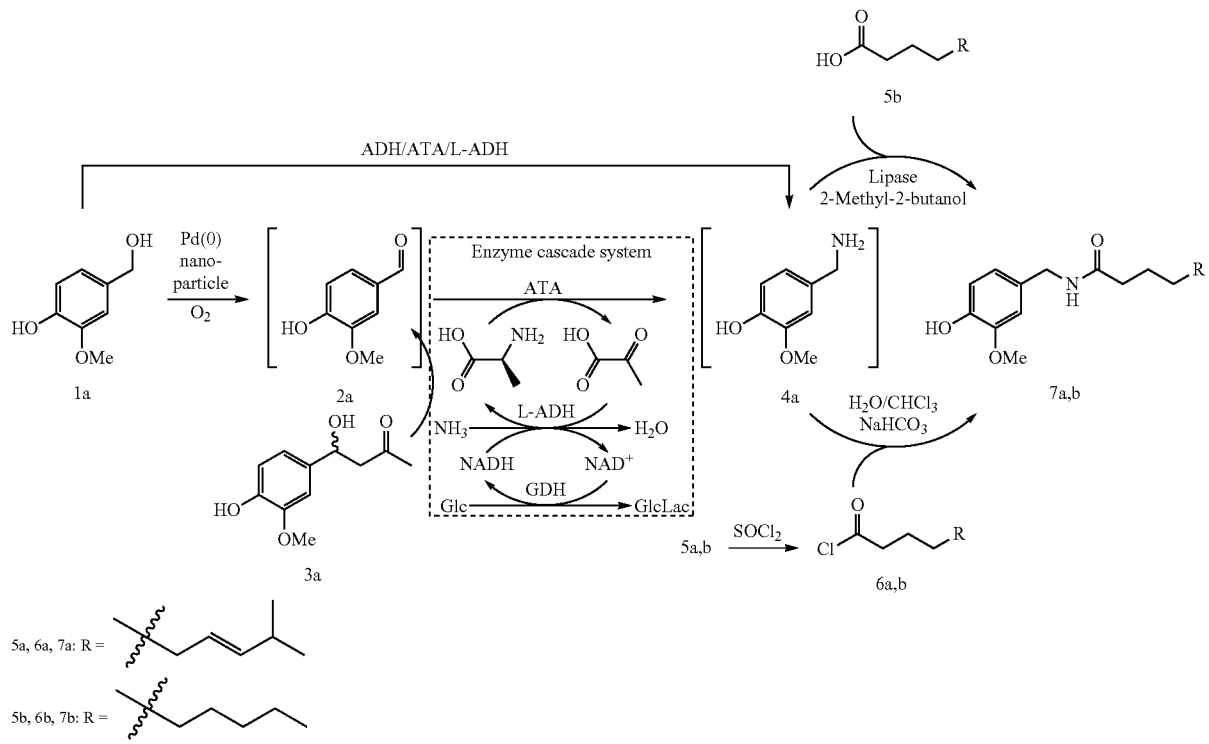

Scheme 4. Schematic overview of the total synthesis of capsaicin and nonivamide.

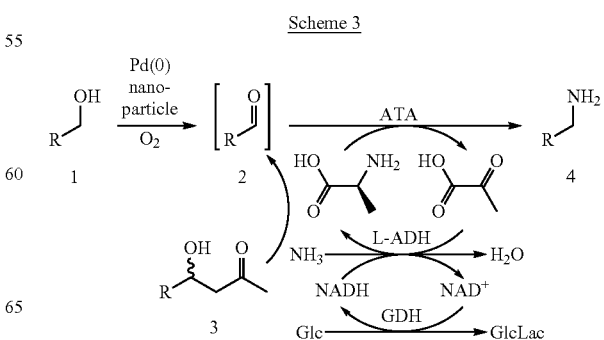

Scheme 3

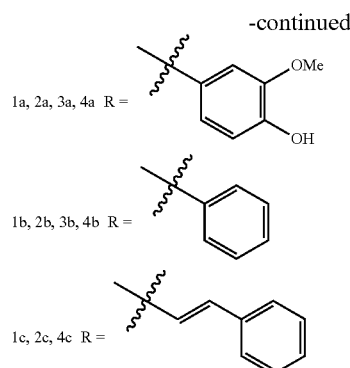

1a, 2a, 3a, 4a R = (4-hydroxy-3-methoxyphenyl)
1b, 2b, 3b, 4b R = (phenyl)
1c, 2c, 4c R = (styryl)

Two other aldehydes, benzaldehyde (2b) and cinnamaldehyde (2c), were successfully converted to the corresponding amines, 4b and 4c respectively, using the same procedure. The reaction compositions were 250 mM L-alanine, 5 mM aldehyde (2b or 2c), 150 mM ammonium chloride, 150 mM D-glucose and 1 mM NADH v/v in HEPES buffer (45 mM, pH 8.2 at 37° C.), with 10% DMSO v/v, together with 1 mg/mL ATA, 7 U/mL L-ADH and 10 U/mL GDH. In 23 h, 4b was obtained with a conversion of 89%, while 4c was obtained with a conversion of 76%.

General Procedure for Synthesis of Capsaicin and Nonivamide from Vanillylamine.

Step 1: A solution of the acid 5a or 5b (19.0 mmol, 1.0 equiv.) and thionyl chloride (9.04 g, 76.0 mmol, 4.0 equiv.) was refluxed for 4 h. The excess thionyl chloride was removed by rotary evaporator and the residual were removed under high vacuum to yield the acyl chloride 6a or 6b as light yellow.[25] The material was used in the next step without further purification.

Step 2: To a vial (8-mL) containing vanillylamine (4) (81.1 mg, 0.53 mmol, 1.00 equiv.) and NaHCO$_3$ (145.6 mg, 1.73 mmol, 3.27 equiv.) was added 1-120 (1.5 mL) and stirred for 30 minutes at r.t., followed by addition of CHCl$_3$ (2 mL) and the reaction kept stirring at r.t. for 15 minutes. Next, a solution of 6a or 6b (0.61 mmol, 1.16 equiv.) in CHCl$_3$ (0.5 mL) was added drop wise and the reaction stirred at r.t. for additional 30 minutes. Afterwards the reaction was heated to 40° C. and stirred for 30 minutes (monitored by TLC). The organic layer was separated and the water layer washed with CHCl$_3$ (3×15 mL). The combined organic layers were washed with aq. HCl (2%) and then brine followed by drying over Na$_2$SO$_4$. The crude material was purified by chromatography to afford the 7a (isolated yield 91%) and 7l) (isolated yield 94%) as light yellow oil.[26]

7a: IR (neat) λ 3296 (br), 2922 (s), 2853 (m), 1730 (m), 1647 (m), 1515 (m), 1459 (m), 1376 (m), 1272 (m), 1214 (m), 1154 (m), 1123 (w), 1034 (m), 970 (w), 816 (w), 756 (s), 667 (m), 557 (w) cm$^{-1}$; $^1$H NMR (500 MHz, CDCl$_3$): δ 6.86 (d, J=8.1 Hz, 1H), 6.81 (s, 1H), 6.79-6.73 (m, 1H), 5.62 (br s, 2H), 5.41-5.27 (m, 1H), 4.36 (d, J=5.7 Hz, 2H), 3.88 (s, 3H), 2.36-2.13 (m, 4H), 1.98 (q, J=8.3 Hz, 1H), 1.83-1.72 (m, 1H), 1.72-1.57 (m, 4H), 1.53-1.43 (m, 1H), 1.42-1.34 (m, 1H), 0.95 (d, J=7.0 Hz, 2H), 0.93 (d, J=6.8 Hz, 3H).

$^{13}$C NMR (125 MHz, CDCl$_3$): δ 172.9, 172.5, 146.8, 145.30, 145.27, 138.3, 130.6, 130.5, 126.6, 121.03, 120.97, 114.52, 114.49, 110.86, 110.81, 72.1, 63.3, 56.12, 56.09, 43.76, 43.69, 36.9, 36.7, 35.1, 32.4, 31.1, 30.5, 29.4, 25.4, 25.2, 22.8, 21.1, 15.1, 14.4; HRMS (ESI$^+$) [M+Na]$^+$ calcd for C$_{18}$H$_{27}$NO$_3$Na$^+$: 306.2064, found: 306.2059.

7b: IR (neat) λ 3293 (br), 2926 (m), 2855 (m), 1641 (m), 1514 (m), 1462 (m), 1432 (m), 1376 (w), 1272 (m), 1214 (m), 1154 (m), 1123 (w), 1036 (m), 909 (m), 853 (w), 749 (s), 666 (m), 556 (w), 464 (w) cm$^{-1}$; $^1$H NMR (500 MHz, CDCl$_3$): δ 6.85 (d, J=8.0 Hz, 1H), 6.80 (s, 1H), 6.75 (d, J=8.2 Hz, 1H), 5.73 (br s, 2H), 4.34 (d, J=5.7 Hz, 2H), 3.86 (s, 3H), 2.19 (t, J=7.7 Hz, 2H), 1.68-1.59 (m, 2H), 1.38-1.18 (m, 10H), 0.87 (t, J=7.0 Hz, 3H).

$^{13}$C NMR (125 MHz, CDCl$_3$): δ 173.1, 146.9, 145.30, 130.5, 120.9, 114.5, 110.8, 56.1, 43.7, 37.0, 31.9, 29.5, 29.3, 25.9, 22.8, 14.2; HRMS (ESI$^+$) [M+Na]$^+$ calcd for C$_{17}$H$_{27}$NO$_3$Na$^+$: 316.1883, found: 316.1879.

Total Synthesis of Nonivamide in One Pot

Step 1: 50 mM vanillin (2a) was used in a 13.06 mL scale, which would give 100 mg vanillylamine (4a) if the conversion is too %. Vanillin was first dissolved in DMSO and then mixed with D-glucose, ammonium chloride and L-alanine in HEPES buffer 50 mM. The pH was adjusted to 8.2 (1 M NaOH) and the solution was mixed with NADH and the enzymes in a 50 mL falcon tube to give the final concentrations 250 mM L-alanine, 50 mM vanillin, 150 mM ammonium chloride, 150 mM D-glucose, 1 mM NADH and 10% DMSO v/v, together with 1.6 mg/mL ATA, 7 U/mL L-alanine dehydrogenase and to U/mL glucose dehydrogenase. The reaction was performed in 37° C. and darkness with no stirring. After 19 h the conversion had reached >99% as determined by HPLC analysis. The solution was stored in −80° C. (total volume 13.01 mL after removal of sample for HPLC) until the second step was performed.

Step 2a: To a flask containing crude reaction mixture from previous enzyme cascade reaction step (volume 13.01 mL, containing vanillylamine (99.6 mg, 0.65 mmol, 1.00 equiv.) was added NaHCO$_3$ (178.9 mg, 2.13 mmol, 3.27 equiv.) and stirred for 30 minutes at r.t., followed by addition of CHCl$_3$ (20 mL) and the reaction kept stirring at r.t. for 15 minutes. Next, a solution of 6b (132.1 mg, 0.75 mmol, 1.16 equiv.) in CHCl$_3$ (5.0 mL) was added drop wise and the reaction stirred at r.t. for additional 30 minutes. Afterwards the reaction was heated to 40° C. and stirred for 30 minutes (monitored by TLC). The organic layer was separated and the water layer washed with CHCl$_3$ (3×50 mL). The combined organic layers were washed with aq. HCl (2%) and then brine followed by drying over Na$_2$SO$_4$. The crude material was purified by chromatography to afford nonivamide (7b) (isolated yield 92%) as light yellow oil.

Step 2b: The dried crude reaction mixture from the previous step (containing vanillylamine 94 mg, 0.62 mmol, 1.00 equiv.) was dissolved in 2-methyl-2-butanol (31 mL, 20 mM). To the reaction was added Ms 4 Å (2 g), compound 5b (98.7 mg, 0.62 mmol, 1.00 equiv.) and lipase (1.9 g, 20 mg/mL). The reaction was stirred at 45° C. for 48 h. Afterwards the reaction was cooled to room temperature and filtered. The solvent was removed under reduced pressure and the crude material was purified by chromatography to afford nonivamide (7b) (isolated yield 52%) as light yellow oil.

Procedure for Synthesis of Vanillylamine from Vanillyl Alcohol

Step 1: An oven dried Microwave vial was loaded with vanillyl alcohol (1a) (46.3 mg, 0.3 mmol, 1.0 equiv.) and Pd(0)-Nanocatalyst (Pd(0)-AmP-MFC, 20.1 mg, 0.015 mmol, 8 wt %) 27 or (Pd(0)-CPG, 500 Å, 90.0 mg, 0.015 mmol, 166 µmol/g, 2 wt %) followed by addition of toluene (0.6 mL). Next, the mixture was sealed and a balloon filled with 02 was connected to the vial and the reaction stirred at 70° C. After 3 h (when Pd(0)-AmP-MFC was used) or 2 h (when Pd(0)-CPG, 500 Å was used) conversion had reached >99% to vanillin (2a).

Vanillin: IR (neat) λ 3335 (br), 3016 (w), 2838 (w), 1668 (m), 1583 (m), 1509 (m), 1461 (w), 1432 (w), 1400 (w), 1265 (s), 1207 (w), 1150 (s), 1118 (m), 1027 (m), 957 (w), 866 (w), 820 (w), 779 (w), 750 (m), 728 (s), 666 (w), 628 (w), 588 (w), 551 (w) cm$^{-1}$; $^1$H NMR (500 MHz, CDCl$_3$): δ 9.82 (s, 1H), 7.43-7.40 (m, 2H), 7.03 (d, J=8.6 Hz, 1H), 6.35 (br s, 1H), 3.95 (s, 3H). $^{13}$C NMR (125 MHz, CDCl$_3$): δ 191.1, 151.9, 147.3, 130.0, 127.7, 114.5, 108.9, 56.2; HRMS (ESI$^+$) [M+H]$^+$ calcd for C$_8$H$_9$O$_3$: 153.0546, found: 153.0544.

Step 2: A few drops of the crude mixture from the previous step, still containing Pd nanoparticles, was transferred to an eppendorf tube and mixed with 200 μL distilled water. To determine the concentration of vanillin in this solution a sample was taken, the Pd nanoparticles in the sample were removed by centrifugation (4000 rpm for 15 min) and HPLC analysis was performed. D-glucose, ammonium chloride and L-alanine were dissolved in HEPES buffer 50 mM, the pH was adjusted to 8.2 (1 M NaOH) and the solution was mixed with NADH and the enzymes and added directly to the tube containing the crude vanillin solution (100 μL). The final reaction volume was 1 mL with concentrations of 250 mM L-alanine, 1.5064 mM vanillin from crude solution, 150 mM ammonium chloride, 150 mM D-glucose, 1 mM NADH, together with 1 mg/mL ATA, 7 U/mL L-alanine dehydrogenase and to U/mL glucose dehydrogenase. The reaction was performed in 37° C. and darkness with no stirring. Before HPLC analysis, any Pd nanoparticles in the sample were removed by centrifugation (4000 rpm for 15 min). After 44 h the reaction had completed and vanillylamine (4a) was obtained with a conversion of 87% as determined by HPLC analysis. This gives an overall conversion of vanillyl alcohol (1a) to vanillylamine (4a) of 87%.

Procedure for Aldol Reaction Between Vanillin and Acetone

To a vial (8-mL) containing vanillin (2a) (114.1 mg, 0.75 mmol, 1.00 equiv.) and acetone (7.5 mL) was added proline (DL-Proline or L-Proline) (26.0 mg, 0.23 mmol, 30 mol %) under N$_2$. The reaction was stirred at r.t. for 24 h, and then quenched by addition of sat. aq. NH$_4$Cl (3.0 mL). The reaction mixture was extracted with ethyl acetate (3×20 mL) and the combined organic phases were washed with brine (10 mL) and dried over Na$_2$SO$_4$. The crude material was purified by chromatography to afford 3 (isolated yield 74%) as yellow oil.28

2: IR (neat) λ 3392 (br), 2924 (m), 1703 (m), 1604 (w), 1515 (m), 1455 (w), 1431 (w), 1363 (w), 1269 (m), 1213 (m), 1153 (m), 1123 (m), 1032 (m), 858 (w), 819 (w), 749 (s), 666 (w), 638 (w), 540 (w) cm$^{-1}$; $^1$H NMR (500 MHz, CDCl$_3$): δ 6.93 (d, J=1.9 Hz, 1H), 6.87 (d, J=8.1 Hz, 1H), 6.80 (dd, J=8.1, 1.9 Hz, 1H), 5.60 (br s, 1H), 5.09 (dt, J=9.2, 3.0, Hz, 1H), 3.90 (s, 3H), 3.23 (d, J=3.0 Hz, 1H), 2.88 (dd, J=17.6, 9.3 Hz, 1H), 2.80 (dd, J=17.6, 3.3 Hz, 1H), 2.20 (s, 3H). $^{13}$C NMR (125 MHz, CDCl$_3$): δ 209.4, 146.8, 145.3, 135.0, 118.7, 114.4, 108.4, 69.9, 56.1, 52.2, 30.9; HRMS (ESI$^+$) [M+Na]$^+$ calcd for C$_{11}$H$_{14}$O$_4$Na$^+$: 233.0784, found: 233.0784.

Alanine-Catalysed Retro-Aldol Reactions

Vanillin (2a) was prepared from the lignin model 3 by a retro-aldol reaction catalysed by alanine. Since this system was to be used with the enzyme cascade system in one pot for the synthesis of vanillylamine (4a), the conditions used for initial experiments on the retro aldol-reaction were the same as the conditions used for the previous synthesis of vanillylamine. HPLC was used for analysis.

Compound 3 was dissolved in DMSO and mixed with L-alanine in HEPES buffer pH 8.2, giving a final volume of 1 mL and concentrations of 2.5 mM of compound 3, 250 mM L-alanine, 45 mM HEPES and 10% DMSO v/v. The reaction was performed in 37° C. for 70 h, after which all 3 had been consumed. At this point 38% of the starting material had been converted to vanillin, and the rest to side products such as the dehydration product of 3 (conversion not determined). A control reaction with no alanine but otherwise identical composition gave vanillin with a conversion of 5.3% with some 3 still in the reaction after 70 h. This shows that there is some spontaneous retro-aldol activity, but it is much slower than the alanine catalyzed reaction. A third reaction with the same composition including alanine but with pH 7 gave vanillin with a conversion of 19% after 70 h, with some 3 still in the reaction. These results are summarized in table 1.

L-alanine is a chiral catalyst and the compound 3 used is racemic. Experiments were made to investigate the use of DL-alanine as catalyst for racemic 3, and the use of L-alanine as a catalyst for (S)-3. A control reaction with L-alanine as catalyst for racemic 3 was also performed for comparison. All reactions were run as previously in 1 mL volume with 45 mM HEPES pH 8.2, DMSO 10% v/v and 2.5 mM of compound 3. 250 mM L-alanine or 500 mM DL-alanine was used as catalyst. After 116 h in room temperature, vanillin was obtained with a conversion of 24% in the control reaction, 30% with the racemic catalyst and 19% with (S)-3 as substrate. These results are summarized in table 1.

TABLE 1

Summary of the alanine-catalysed retro-aldol reactions performed.

| Substrate (2.5 mM) | Catalyst | pH | Temp (° C.) | Time (h) | Conversion to vanillin (%) |
|---|---|---|---|---|---|
| Racemic 3 | 250 mM L-alanine | 8.2 | 37 | 70 | 38 |
| Racemic 3 | none | 8.2 | 37 | 70 | 5.3 |
| Racemic 3 | 250 mM L-alanine | 7 | 37 | 70 | 19 |
| Racemic 3 | 250 mM L-alanine | 8.2 | r.t | 116 | 24 |
| Racemic 3 | 500 mM DL-alanine | 8.2 | r.t | 116 | 30 |
| (S)-3 | 250 mM L-alanine | 8.2 | r.t | 116 | 19 |

Procedure for Synthesis of Vanillylamine by a Retro-Aldol Reaction Followed by Transamination in One Pot D-glucose, ammonium chloride and L-alanine were dissolved in HEPES buffer 50 mM and the pH was adjusted to 8.2 (1 M NaOH). The lignin model 3 was dissolved in DMSO and then added to the solution together with NADH and the enzymes to give the final volume 1 mL and concentrations 250 mM L-alanine, 2.5 mM of compound 3, 150 mM ammonium chloride, 150 mM D-glucose, 1 mM NADH and 10% DMSO v/v, together with 1 mg/mL ATA, 7 U/mL L-alanine dehydrogenase and 10 U/mL glucose dehydrogenase. The reaction was performed in 37° C. and darkness with no stirring. This resulted in a conversion to vanillylamine (4a) of 25% after 92 h as determined by HPLC analysis.

The same reaction was repeated but using too mM HEPES instead of 50 mM (final volume 1 mL and concentrations 250 mM L-alanine, 2.5 mM of compound 3, 150 mM ammonium chloride, 150 mM D-glucose, 1 mM NADH and to % DMSO v/v, together with 0.9 mg/mL ATA, 7 U/mL L-alanine dehydrogenase and to U/mL glucose dehydrogenase). The reaction was performed in 37° C. and darkness with no stirring. This resulted in a conversion to vanillylamine (4a) of 40% after 90 h as determined by HPLC analysis.

The effect of the higher buffer concentration was investigated on the previously described system for synthesis of vanillylamine (4a) from vanillin (2a). In the same way as earlier, vanillin was dissolved in DMSO and then mixed with D-glucose, ammonium chloride and L-alanine in HEPES buffer too mM. The pH was adjusted to 8.2 (1 M NaOH) and the solution was mixed with NADH and the enzymes in an eppendorf tube to give the final volume 1 mL and concentrations 250 mM L-alanine, 50 mM vanillin, 150 mM ammonium chloride, 150 mM D-glucose, 1 mM NADH and to % DMSO v/v, together with 0.9 mg/mL ATA, 7 U/mL L-alanine dehydrogenase and to U/mL glucose dehydrogenase. The reaction was performed in 37° C. and darkness with no stirring. This resulted in the reaction ending after 18 h, with a conversion of vanillin to vanillylamine of only 77%. Since conversions of 95% (small scale) and >99% (scale-up) were obtained with the same system with a lower buffer concentration, it was decided to not work further with the too mM buffer concentration.

Synthesis of 7-phenylhept-6-ynoic acid[29]

To an oven dried flask were added Pd(PPh$_3$)$_4$ (173.3 mg, 0.15 mmol, 3 mol %) and CuI (19.0 mg, 0.1 mmol, 2 mol %) and the flask was flushed under N$_2$ for 5 minutes, followed by addition of hept-6-ynoic acid (630.8 mg, 5 mmol, 1.0 equiv.), 1-iodobenzene (1.22 g, 6 mmol, 1.2 equiv.) and triethylamine (20 mL). The reaction was heated to 50° C. and stirred for 16 h. Afterwards the crude material was concentrated and Ethyl acetate (100 mL) and aq. HCl (1M, 20 mL) were added and extracted. The water phase was extracted again with Ethyl acetate (100 mL) and the combined organic layers were drying over Na$_2$SO$_4$ and concentrated. The crude material was purified by chromatography to afford 7-phenylhept-6-ynoic acid (isolated yield 82%) as brown solid.

$^1$H NMR (500 MHz, CDCl$_3$): δ 10.75 (br s, 1H), 7.43-7.36 (m, 2H), 7.32-7.22 (m, 3H), 2.45 (t, J=7.1 Hz, 4H), 1.88-1.78 (m, 2H), 1.72-1.63 (m, 2H).

Synthesis of Phenylcapsaicin

To an oven dried vial containing Ms 4 Å (100 mg), were added 2-methyl-2-butanol (5 mL), 7-phenylhept-6-ynoic acid (20.2 mg, 0.1 mmol, 1.0 equiv.), 4a (15.2 mg, 0.1 mmol, 1.0 equiv.), and Novozyme (100 mg). The reaction was stirred at 45° C. for 48 h. Afterwards the reaction was cooled to room temperature and filtered. The solvent was removed under reduced pressure and the crude material was purified by chromatography to afford phenylcapsaicin (isolated yield 95%) as light yellow oil.

IR (neat)×3053 (w), 2937 (w), 1645 (m), 1600 (w), 1513 (m), 1461 (w), 1431 (m), 1373 (m), 1264 (m), 1236 (w), 1154 (m), 1123 (m), 1034 (m), 854 (w), 818 (w), 732 (s), 693 (m), 542 (w), 465 (w) cm$^{-1}$; $^1$H NMR (500 MHz, CDCl$_3$): δ 7.39-7.33 (m, 2H), 7.29-7.24 (m, 3H), 6.85 (d, J=8.0 Hz, 1H), 6.80 (s, 1H), 6.75 (d, J=8.1 Hz, 1H), 5.67 (br s, 1H), 5.60 (s, 1H), 4.36 (d, J=5.7 Hz, 2H), 3.86 (s, 3H), 2.44 (t, J=7.0 Hz, 2H), 2.27 (t, J=7.1 Hz, 2H), 1.88-1.80 (m, 2H), 1.69-1.61 (m, 2H).

$^{13}$C NMR (125 MHz, CDCl$_3$): δ 172.5, 146.8, 145.3, 131.7, 130.5, 128.4, 127.8, 123.9, 121.0, 114.5, 110.8, 89.8, 81.2, 56.1, 43.7, 36.4, 28.4, 25.2, 19.4; HRMS (ESI$^+$) [M+Na]$^+$ calcd for C$_{21}$H$_{23}$NO$_3$Na$^+$: 360.1572, found: 360.1570.

Different Oxidation-Amination Cascades
Method 1 (DABCO-CuCl-TEMPO Method)

A microwave-vial containing a solution of CuCl (0.495 mg, 0.05 mmol, 5 mol %) and DABCO (0.56 mg, 0.05 mmol, 5 mol %) in toluene (0.25 mL) was stirred at RT for to min. Afterwards, TEMPO (0.78 mg, 0.015 mmol, 5 mol %) was added to the reaction mixture and stirred for 5 min. Then, alcohol (0.1 mmol) was added and a balloon containing oxygen gas was connected to the vial. The mixture was heated to too ° C. and stirred for 2 hours at this temperature.

Method 2 (CuCl-bipyridyl-TEMPO Method)

A microwave-vial containing a solution of CuCl (0.495 mg, 0.05 mmol, 5 mol %) and bipyridyl (0.8 mg, 0.05 mmol, 5 mol %) in toluene (0.25 mL) was stirred at RT for 10 min. Afterwards, TEMPO (0.78 mg, 0.015 mmol, 5 mol %) was added to the reaction mixture and stirred for 5 min. Then, alcohol (0.1 mmol) was added and a balloon containing oxygen gas was connected to the vial. The mixture was heated to 100° C. and stirred for 16 hours at this temperature.

Method 3 (Palladium Nanocatalyst Method)

Alcohol (0.1 mmol) was added to a microwave-vial containing Pd(0)-Nanocatalyst (Pd(0)-AmP-MFC, 6.7 mg, 0.05 mmol, 8 wt %, 5 mol %) in toluene (0.35 mL) and a balloon containing oxygen gas was connected to the vial. The mixture was heated to 70° C. and stirred for 16 hours at this temperature.

Method 4 (Meal-Free Oxidation)

A solution of KBr (1.2 mg, 0.01 mmol, to mol %) in water (1 mL) was added to a microwave-vial containing a solution of alcohol (0.1 mmol, 1.0 equiv.) and TEMPO (1.6 mg, 0.01 mmol, 10 mol %) in CH$_2$CL$_2$ (4 mL) and stirred at 0° C. Then, a solution of NaOCl (5.3 g, to mmol, too equiv.) with pH 9 was added drop by drop to the reaction mixture. Afterwards, NaOH (2M, 3 mL) was added and a balloon containing oxygen gas was connected to the vial. The mixture was stirred at 0° C. for 3 h.

After performing methods 1-4, DMSO was added to the vial. L-Alanine, ammonium chloride and D-glucose were dissolved in 50 mM HEPES buffer, the pH was adjusted to 8.2 at 37° C. and the solution was added to the reaction vial. Next, NADH, GDH, L-ADH and ATA were dissolved in HEPES buffer (50 mM, pH 8.2 at 37° C.) and added to the reaction vial to give final concentrations of 250 mM L-alanine, 150 mM ammonium chloride, 150 mM D-glucose, 1 mM NADH, 7 U/mL L-ADH, to U/mL GDH and 2 mg/mL ATA. The concentration of aldehyde starting material, the amounts of DMSO and toluene in the reaction and the total volume were different for each reaction performed, and are summarized in table X. The reactions were kept in 37° C. and darkness with no stirring. After 24 h, the conversion was determined by HPLC (table 2).

TABLE 2

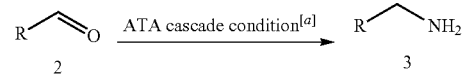

TABLE 2-continued

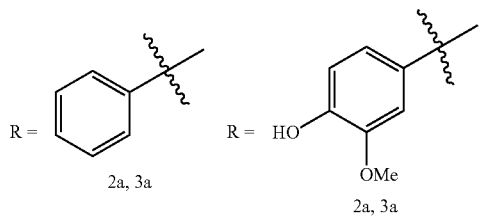 [SMILES: *c1ccccc1 ; *c1ccc(O)c(OC)c1]

| Entry | Aldehyde | Oxidation catalyst[b] | Buffer solution (mL) | DMSO (mL) | Toluene (mL) | Product |
|---|---|---|---|---|---|---|
| 1 | 2a, 0.1 mmol, 20 mM | CuCl, bipyridyl, TEMPO | 4.7 | 0.30 | 0.20 | 3a, c = 33% |
| 2 | 2a, 0.1 mmol, 14 mM | Pd(0)-MCF | 6.7 | 0.37 | 0.33 | 3a, c = 46% |
| 3 | 2b, 0.1 mmol, 20 mM | CuCl, bipyridyl, TEMPO | 4.7 | 0.30 | 0.20 | 3b, c = 32% |
| 4 | 2b, 0.1 mmol, 12 mM | Pd(0)-MCF | 7.8 | 0.50 | 0.33 | 3b, c = 20% |

[a]ATA, L-ADH, GDH, L-alanine, ammonium chloride, D-glucose, NADH, HEPES, DMSO, $H_2O$.
[b]These compounds were left in the vial from the previous oxidation step.

Influence of Toluene

The influence of toluene on the performance of the ATA/L-ADH/GDH cascade system was investigated. Reactions where benzaldehyde was converted to benzylamine by the cascade system were run with different amounts of toluene. Benzaldehyde was first dissolved mixtures of toluene and DMSO (table Y) and added to 1.5 mL eppendorf tubes. L-Alanine, ammonium chloride and D-glucose were dissolved in 50 mM HEMS buffer, the pH was adjusted to 8.2 at 37° C. and the solution was added to the reaction tubes. Next, NADH, GDH, L-ADH and ATA were dissolved in HEPES buffer (50 mM, pH 8.2 at 37° C.) and added to the reaction tubes to give final concentrations of 20 mM benzaldehyde, 250 mM L-alanine, 150 mM ammonium chloride, 150 mM D-glucose, 1 mM NADH, 7 U/mL L-ADH, to U/mL GDH and 1 mg/mL ATA. The total volume of each reaction was 1 mL, where 10% v/v was the DMSO/toluene mixture. Reactions were kept in 37° C. and darkness with no stirring. Conversions were determined by HPLC after 1, 2, 4, 6 and 24 hours. All reactions had finished after 4 hours, and the results are summarized in table 3.

TABLE 3

| Entry | Toluene (% v/v)[a] | Conversion (%)[b] |
|---|---|---|
| 1 | 0 | 90 |
| 2 | 0.5 | 88 |
| 3 | 1 | 78 |
| 4 | 2 | 72 |
| 5 | 5 | 72 |

[a]% v/v total reaction volume.
[b]Determined by HPLC after 4 h.

Influence of Pd(0)-MCF

The influence of Pd(0)-MCF on the performance of the ATA/L-ADH/GDH cascade system was investigated. Reactions where benzaldehyde was converted to benzylamine by the cascade system were run with different amounts of Pd(0)-MCF. The palladium nanoparticles were first added to 1.5 mL eppendorf tubes (table Z). Benzaldehyde was dissolved in DMSO and added to the tubes. L-Alanine, ammonium chloride and D-glucose were dissolved in 50 mM HEPES buffer, the pH was adjusted to 8.2 at 37° C. and the solution was added to the reaction tubes. Next, NADH, GDH, L-ADH and ATA were dissolved in HEPES buffer (50 mM, pH 8.2 at 37° C.) and added to the reaction tubes to give final concentrations of 5 mM benzaldehyde, 250 mM L-alanine, 150 mM ammonium chloride, 150 mM D-glucose, 1 mM NADH, 7 U/mL L-ADH, to U/mL GDH and 1 mg/mL ATA. The total volume of each reaction was 1 mL with 10% v/v DMSO. Reactions were kept in 37° C. and darkness with no stirring. Conversions were determined by HPLC after 1, 2, 4, 6 and 24 hours. All reactions had finished after 4 hours, and the results are summarized in table 4.

TABLE 4

| Entry | Pd(O)-MCF (mg/mL) | Conversion (%)[a] |
|---|---|---|
| 1 | 0 | 88 |
| 2 | 0 | 83 |
| 3 | 0.1 | 85 |
| 4 | 0.6 | 83 |
| 5 | 1.1 | 78 |
| 6 | 2 | 79 |

[a]Determined by HPLC after 4 h.

REFERENCES

1. E. K. Nelson, J. Am. Chem. Soc., 1919, 41, 1115-1121.
2. D. J. Bennett and G. W. Kirby, J. Chem. Soc. C, 1968, 442-446.
3. K. Iwai, T. Suzuki and H. Fujiwake, Agric. Biol. Chem., 1979, 43, 2493-2498.
4. T. Kawada, T. Watanabe, K. Katsura, H. Takami and K. Iwai, J. Chromatogr., 1985, 329, 99-105.
5. A. Kobayashi, T. Osaka, Y. Namba, S. Inoue, T. H. Lee and S. Kimura, Am. J. Physiol. Regul. Integr. Comp. Physiol., 1998, 275, R92-R98
6. T. Watanabe, T. Kawada, T. Kato, T. Harada and K. Iwai, Life Sciences, 1994, 54, 369-374.
7. K. Kim, T. Kawada, K. Ishihara, K. Inoue and T. Fushiki, Biosci. Biotechnol. Biochem., 1997, 61, 1718-1723.
8. T. Kawada, K. Hagihara and K. Iwai, J. Nutr., 1986, 116, 1272-1278
9. K. Bley, G. Boorman, B. Mohammad, D. McKenzie and S. Babbar, Toxicol. Pathol., 2012, 40, 847-873.
10. Y. Surh, J. Natl. Cancer Inst., 2002, 94, 1263-1265.

11. A. Oyagbemi, A. Saba, O. Azeez, Indian J. Cancer, 2010, 47, 53-58
12. E. K. Nelson, J. Am. Chem. Soc., 1919, 41, 2121-2130.
13. K. Abiraj and D. C. Gowda, J. Chem. Res. (S), 2003, 6, 332-334
14. P. M. Gannett, D. L. Nagel, P. J. Reilly, T. Lawson, J. Sharpe and B. Toth, J. Org. Chem., 1988, 53, 1064-1071.
15. 11 Kaga, M. Miura and K. Orito, J. Org. Chem., 1989, 54, 3477-3478.
16. B. Wang, F. Yang, Y. Shan, W. Qiu and J. Tang, Tetrahedron, 2009, 65, 5409-5412.
17. K. Kobata, K. Yoshikawa, M. Kohashi and T. Watanabe, Tetrahedron lett., 1996, 37, 2789-2790.
18. K. Kobata, M. Toyoshima, M. Kawamura and T. Watanabe, Biotechnol. Lett., 1998, 20, 781-783.
19. M. Koreishi, D. Zhang, H. Imanaka, K. Imamura, S. Adachi, R. Matsuno and K. Nakanishi, J. Agric. Food. Chem., 2006, 54, 72-78.
20. E. Castillo, A. Torres-Gavilan, P. Severiano, N. Arturo and A. López-Munguía, Food Chem., 2007, 100, 1202-1208.
21. Vannillin is produced from wood in 1,500 tonnes every year by Borregaard. Life-Cycle Assessment proves that wood derived vanillin has a 90% smaller CO2-footprint as compared to mineral oil-based vanillin. (http://sustain-ableifra.wordpress.com/2012/06/11/vanillin-extracted-from-wood-at-borregaard/)
22. S. R. Collinson and W. Thielemans, Coord. Chem. Rev., 2010, 254, 1854-1870.
23. Esposito, Lawrence J.; K. Formanek, G. Mentz, F. Mauger, V. Maureaux, G. Robert, and F. Truchet (1997). "Vanillin". Kirk-Othmer Encyclopedia of Chemical Technology, 4th edition
24. New York: John Wiley & Sons. pp. 812-825.
24. K. E. Cassimjee, M. S. Humble, V. Miceli, C. G. Colomina and P. Berglund, ACS Catal., 2011, 1, 1051-1055.
25. J. Zhao, T. D. Gover, S. Muralidharan, D. A. Auston, D. Weinreich and J. P. Y. Kao, Bio-chemistry. 2006, 45, 4915-4926
26. B. Wang, F. Yang, Y. Shan, W. Qiu, J. Tang, Tetrahedron, 2009, 65, 5409-5412
27. 27a) E. W. Ping, R. Wallace, J. Pierson, T. F. Fuller and C. W. Jones, Micropor. Mesopor. Mater., 2010, 132, 174-180 27 b) M. Shakeri, C. Tai, E. Göthelid, S. Oscarsson and J. Bäckvall, Chem. Eur. J., 2011, 17, 13269-13273. 27c) E. V. Johnston, O. Verho, M. D. Kärkäs, M. Shakeri, C. Tai, P. Palmgren, K. Eriksson, S. Oscarsson and J. Backvall, Chem. Eur. J., 2012, 18, 12202-12206 27d) L. Deiana, S. Afewerki, C. Palo-Nieto, O. Verho, E. V. Johnston and A. Cordova, Sci. Rep., 2012, 2, 851.; DOI:10.1038/srepoo851
28. M. Edin, J. Bäckvall and A. Córdova, Tetrahedron Lett., 2004, 45, 7697-7701
29. T. Patil, N.; Huo, Z.; B. Bajracharya, G.; Yamamoto, Y., J. Org. Chem. 2006, 71, 3612.

The invention claimed is:

1. A method for one pot conversion of an alcohol to an amide comprising:
a. Converting said alcohol to an aldehyde or a ketone, wherein said alcohol is selected from the group consisting of: (i) vanillyl alcohol, (ii) benzyl alcohols, (iii) cinnamyl alcohols, and (iv) hydroxyl-, methoxy-, and ethoxybenzyl alcohols,
b. Converting said aldehyde or ketone to an amine, wherein the conversion of said aldehyde or ketone to amine is catalyzed by an enzyme cascade system, and
c. Converting said amine to said amide,
wherein said enzyme cascade system comprises Amine Transaminase (ATA) isolated from *Chromobacterium violaceum* and an amine donor catalyst; and
wherein said method is performed in one pot,
wherein said alcohol is converted into said aldehyde or said ketone using a Pd(0) nanoparticle, and
wherein said Pd(0) nanoparticle is selected from the group consisting of Pd(0)-AmP-MFC and Pd(0)-CPG.

2. The method according to claim 1, wherein said enzyme cascade system further comprises ATA, L-alanine as amine donor, NH3, L-alanine dehydrogenase and NADH.

3. The method according to claim 1, wherein:
said alcohol is a primary alcohol,
said aldehyde comprises an R group wherein R is chosen from the group consisting of alkyl, aryl, cinnamyl and heterocyclic,
said amine comprises an R group wherein R is chosen from the group consisting of alkyl, aryl, cinnamyl and heterocyclic, and
said amide comprises (i) an R group wherein R is chosen from the group consisting of alkyl, aryl, cinnamyl and heterocyclic, and (ii) an acyl group (COR$^3$) wherein R$^3$ is chosen from the group consisting of alkyl and aryl.

4. The method according to claim 2, wherein an amine donor catalyst is selected from the group consisting of alanine, IPA (isopropylamine) and methylbenzyl amine.

5. The method according to claim 3, wherein said primary alcohol is selected from a compound of formula 1:

wherein R is selected from the group consisting of:
i.

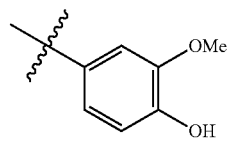 [SMILES: *c1ccc(O)c(OC)c1]

and said primary alcohol thereby being a compound of formula 1a,
ii.

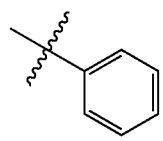 [SMILES: *c1ccccc1]

and said primary alcohol thereby being a compound of formula 1b, and iii.

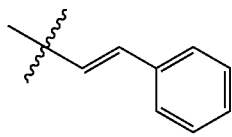 [SMILES: */C=C/c1ccccc1]

and said primary alcohol thereby being a compound of formula 1c.

6. The method according to claim 1, wherein said aldehyde is selected from a compound of formula 2:

2 wherein R is selected from the group consisting of:
i.

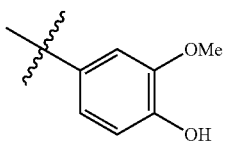 [SMILES: *c1ccc(O)c(OC)c1]

and said aldehyde thereby being a compound of formula 2a,
ii.

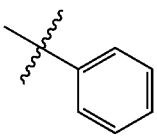

and said aldehyde thereby being a compound of formula 2b, and
iii.

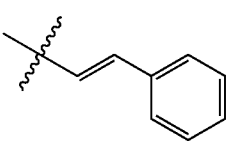 [SMILES: */C=C/c1ccccc1]

and said aldehyde thereby being a compound of formula 2c.

7. The method according to claim 1, wherein said amine is selected from a compound of formula 4:

4 wherein R is selected from the group consisting of:
i.

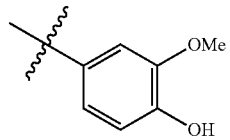 [SMILES: *c1ccc(O)c(OC)c1]

and said amine thereby being a compound of formula 4a,
ii.

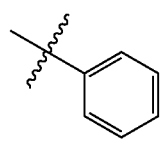 [SMILES: *c1ccccc1]

and said amine thereby being a compound of formula 4b, and
iii.

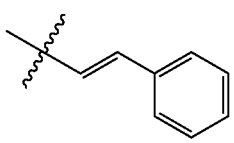 [SMILES: */C=C/c1ccccc1]

and said amine thereby being a compound of formula 4c.

8. The method according to claim 1, comprising:
a. Converting said alcohol to said aldehyde,
wherein said aldehyde is selected from a compound of formula 2:

2 wherein R is selected from the group consisting of:
i.

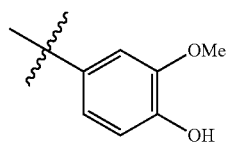 [SMILES: *c1ccc(O)c(OC)c1]

and said aldehyde thereby being a compound of formula 2a,
ii.

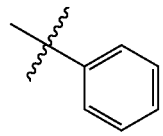

and said aldehyde thereby being a compound of formula 2b, and iii.

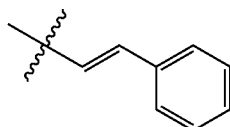

and said aldehyde thereby being a compound of formula 2c, and
wherein said alcohol is selected from the group consisting of a primary alcohol and an aldol,
wherein said primary alcohol is selected from a compound of formula 1:

1 wherein R is selected from the group consisting of:
i.

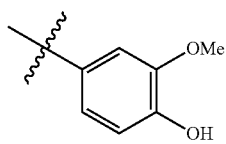 [SMILES: *c1ccc(O)c(OC)c1]

and said primary alcohol thereby being a compound of formula 1a,
ii.

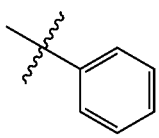

and said primary alcohol thereby being a compound of formula 1b, and
iii.

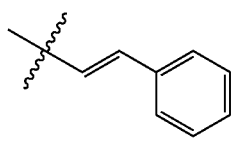 [SMILES: */C=C/c1ccccc1]

and said primary alcohol thereby being a compound of formula 1c,
wherein said aldol is selected from a compound of formula 3:

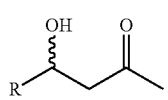

3 wherein R is selected from the group consisting of:
i.

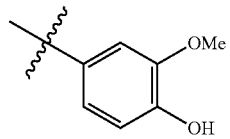 [SMILES: *c1ccc(O)c(OC)c1]

and said aldol thereby being a compound of formula 3a,
ii.

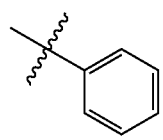 [SMILES: *c1ccccc1]

and said aldol thereby being a compound of formula 3b, and
iii.

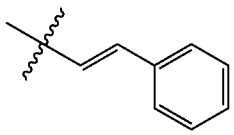

and said aldol thereby being a compound of formula 3c, or
b. Converting said aldehyde according to formula 2a, 2b or 2c to a corresponding amine, wherein said amine is selected from a compound of formula 4:

4 wherein R is selected from the group consisting of:
i.

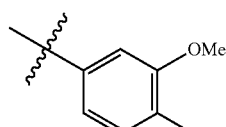

and said amine thereby being a compound of formula 4a,
ii.

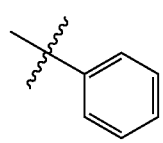 [SMILES: *c1ccccc1]

and said amine thereby being a compound of formula 4b, and iii.

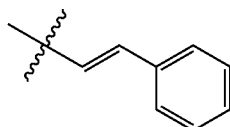

and said amine thereby being a compound of formula 4c,
  wherein the conversion of aldehyde to amine is catalyzed by said enzyme cascade system, and
c. Converting said amine according to formula 4a, 4b, or 4c to an amide, wherein this conversion is carried out in the presence of an acylating agent, wherein said acylating agent is selected from the group consisting of:
  i. compound 5:

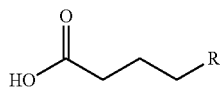

wherein compound 5 is of formula 5a, when R group is

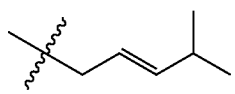 [SMILES: *C/C=C/C(C)C]

and of formula 5b, when R group is

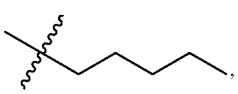 [SMILES: *CCCCC]

respectively;
  ii. compound 6:
    wherein compound 6 is of formula 6a, when R group is

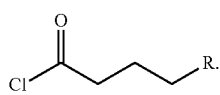

and of formula 6b, when R group is

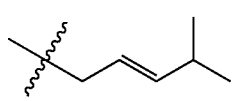 [SMILES: *C/C=C/C(C)C]

respectively; and
  iii. 7-phenylhept-6-yonic acid.

9. The method according to claim 8, wherein the converting said alcohol to said aldehyde of formula, 2a, 2b or 2c, respectively, is carried out in the presence of Pd(0) nanoparticles.

10. The method according to claim 9, wherein the converting
  said amine according to formula 4a, 4b, or 4c to an amide is carried out in the presence of:
    i. said compounds of formula 6a or 6b, respectively, or
    ii. 7-phenylhept-6-yonic acid
  wherein a compound of formula 6a is

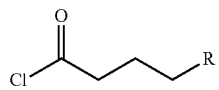

and R is

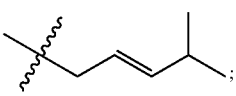 [SMILES: *C/C=C/C(C)C]

and
wherein a compound of formula 6b is

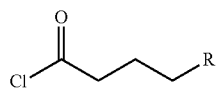

and R is

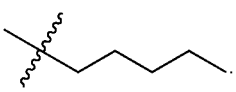 [SMILES: *CCCCC]

11. The method according to claim 1, wherein:
  said alcohol is vanillyl alcohol,
  said aldehyde is vanillin,
  said amine is vanillylamine, and
  said amide is selected from the group consisting of capsaicin, nonivamide, and phenylcapsaicin, and derivates thereof.

12. The method according to claim 11, wherein the converting said vanillyl alcohol to said vanillin is carried out in the presence of Pd(0) nanoparticles,
  wherein said enzyme cascade system further comprises one or more of D-Glucose, glucose dehydrogenase, L-alanine, NH₃, L-alanine dehydrogenase, and NADH, and
  wherein the converting said vanillylamine
    to capsaicin or nonivamide is carried out in the presence of an acylating agent,
    wherein said acylating agent is selected from the group consisting of:
      i. a compound of formulae:

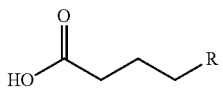

wherein R group is selected from the group consisting of:
a.

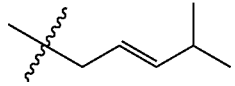 [SMILES: *C/C=C/C(C)C]

thereby being a compound of formula 5a;
b.

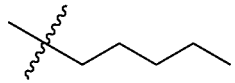 [SMILES: *CCCCC]

thereby being a compound of formula 5b; and
 ii. a compound of formula:

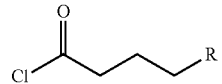

wherein R group is selected from the group consisting of:
a.

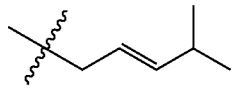 [SMILES: *C/C=C/C(C)C]

thereby being a compound of formula 6a; and
b.

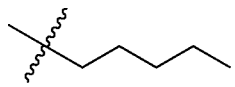 [SMILES: *CCCCC]

thereby being a compound of formula 6b or;
 to phenylcapsaicin is carried out in the presence of 7-phenylhept-6-yonic acid.

13. The method according to claim 12, wherein the converting vanillylamine to capsaicin or nonivamide is carried out in the presence of compounds of formula 6a or 6b, respectively.

14. The method according to claim 11,
 wherein said enzyme cascade system further comprises one or more of alcohol dehydrogenase (ADH) and L-ADH, and
 wherein the converting said vanillylamine
  to capsaicin or nonivamide is carried out in the presence of an acylating agent, wherein said acylating agent is selected from the group consisting of:
   i. a compound of formula:

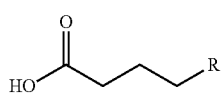

wherein R group is selected from the group consisting of:
a.

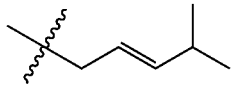 [SMILES: *C/C=C/C(C)C]

thereby being a compound of formula 5a; and
b.

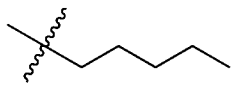 [SMILES: *CCCCC]

thereby being a compound of formula 5b; and
 ii. a compound of formula:

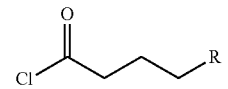

wherein R group is selected from the group consisting of:
a:

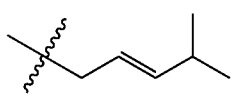 [SMILES: *C/C=C/C(C)C]

thereby being a compound of formula 6a, and
b:

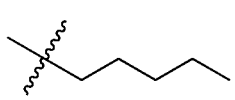

thereby being a compound of formula 6b, or;
 to phenylcapsaicin is carried out in the presence of 7-phenylhept-6-yonic acid.

15. The method according to claim 9, wherein said Pd(0) nanoparticle is selected from the group consisting of Pd(0)-AmP-MFC and Pd(0)-CPG.

16. The method according to claim 1, wherein said amide is selected from the group consisting of capsaicin, nonivamide, phenylcapsaicin, natural capsaicinoids, and non-natural capsaicinoids.

17. The method according to claim 1, wherein said amide is selected from the group consisting of capsaicin, nonivamide, phenylcapsaicin, natural capsaicinoids, and non-natural capsaicinoids according to formula:

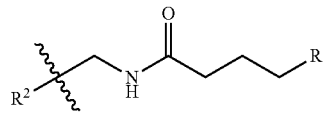

wherein R is selected from the group consisting of

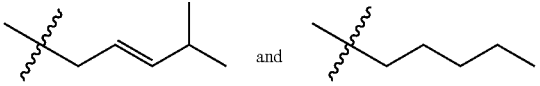

and
wherein R² is selected from the group consisting of

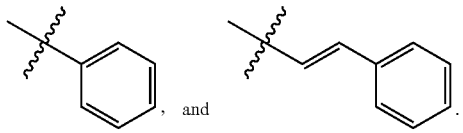 [SMILES: *c1ccccc1 ; */C=C/c1ccccc1]

18. The method according to claim 11, wherein said vanillyl alcohol is derived from lignin.

19. The method according to claim 1, wherein said method is performed in one pot without any purification of intermediates.

20. A method for one pot conversion of an alcohol to an amine comprising:
   a. Converting said alcohol to an aldehyde or a ketone, wherein said alcohol is selected from the group consisting of: (i) vanillyl alcohol, (ii) benzyl alcohols, (iii) cinnamyl alcohols, and (iv) hydroxyl-, methoxy-, and ethoxybenzyl alcohols, and
   b. Converting said aldehyde or ketone to an amine, wherein the conversion of said aldehyde or ketone to amine is catalyzed by an enzyme cascade system,
   wherein said enzyme cascade system comprises Amine Transaminase (ATA) isolated from *Chromobacterium violaceum* and an amine donor catalyst, and
   wherein said method is performed in one pot,
   wherein said alcohol is converted into said aldehyde or said ketone using a Pd(0) nanoparticle, and
   wherein said Pd(0) nanoparticle is selected from the group consisting of Pd(0)-AmP-MFC and Pd(0)-CPG.

21. The method according to claim 20, wherein said enzyme cascade system further comprises an ATA, L-alanine as amine donor, NH₃, L-alanine dehydrogenase and NADH.

22. The method according to claim 20, wherein:
said alcohol is a primary alcohol,
said aldehyde comprises an R group wherein R is chosen from the group consisting of alkyl, aryl, cinnamyl and heterocyclic, and
said amine comprises an R group wherein R is chosen from the group consisting of alkyl, aryl, cinnamyl and heterocyclic.

23. The method according to claim 21, wherein an amine donor catalyst is selected from the group consisting of alanine, IPA (isopropylamine) and methylbenzyl amine.

24. The method according to claim 22, wherein said primary alcohol is selected from a
   compound of formula 1:

wherein R is selected from the group consisting of:
i.

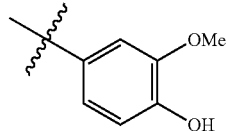 [SMILES: *c1ccc(O)c(OC)c1]

and said primary alcohol thereby being a compound of formula 1a,
   ii.

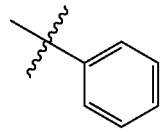 [SMILES: *c1ccccc1]

and said primary alcohol thereby being a compound of formula 1b, and
   iii.

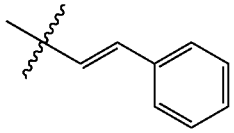 [SMILES: */C=C/c1ccccc1]

and said primary alcohol thereby being a compound of formula 1c.

25. The method according to claim 20, wherein said aldehyde is selected from a compound of formula 2:

wherein R is selected from the group consisting of:
i.

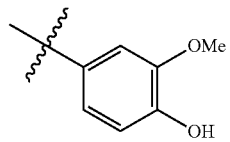

and said aldehyde thereby being a compound of formula 2a,
   ii.

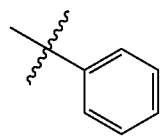 [SMILES: *c1ccccc1]

and said aldehyde thereby being a compound of formula 2b, and iii.

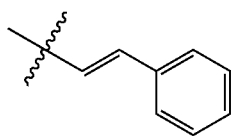 [SMILES: */C=C/c1ccccc1]

and said aldehyde thereby being a compound of formula 2c.

26. The method according to claim 20, wherein said amine is selected from a compound of formula 4:

4 wherein R is selected from the group consisting of:
i.

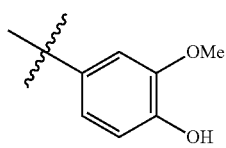 [SMILES: *c1ccc(O)c(OC)c1]

and said amine thereby being a compound of formula 4a,
ii.

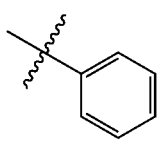 [SMILES: *c1ccccc1]

and said amine thereby being a compound of formula 4b, and
iii.

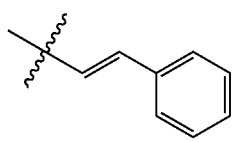 [SMILES: */C=C/c1ccccc1]

and said amine thereby being a compound of formula 4c.

27. The method according to claim 20, comprising:
a. Converting said alcohol to said aldehyde,
   wherein said aldehyde is selected from a compound of formula 2:

2 wherein R is selected from the group consisting of:
iv.

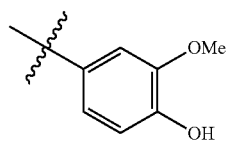 [SMILES: *c1ccc(O)c(OC)c1]

and said aldehyde thereby being a compound of formula 2a,
v.

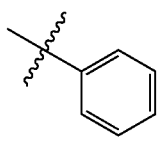 [SMILES: *c1ccccc1]

and said aldehyde thereby being a compound of formula 2b, and
vi.

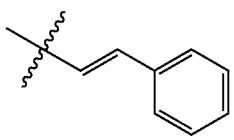 [SMILES: */C=C/c1ccccc1]

and said aldehyde thereby being a compound of formula 2c, and
wherein said alcohol is selected from the group consisting of a primary alcohol and an aldol,
wherein said primary alcohol is selected from a compound of formula 1:

1 wherein R is selected from the group consisting of:
i.

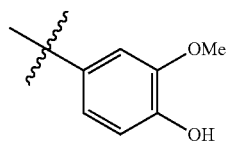

and said primary alcohol thereby being a compound of formula 1a,
ii.

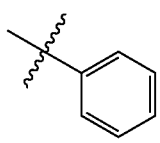 [SMILES: *c1ccccc1]

and said primary alcohol thereby being a compound of formula 1b, and
iii.

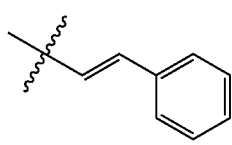 [SMILES: */C=C/c1ccccc1]

and said primary alcohol thereby being a compound of formula 1c,
wherein said aldol is selected from a compound of formula 3:

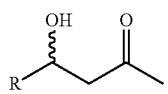

wherein R is selected from the group consisting of:
i.

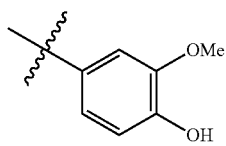 [SMILES: *c1ccc(O)c(OC)c1]

and said aldol thereby being a compound of formula 3a,
ii.

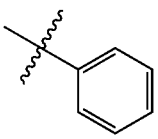

and said aldol thereby being a compound of formula 3b, and
iii.

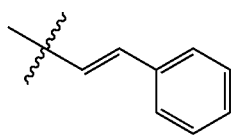 [SMILES: */C=C/c1ccccc1]

and said aldol thereby being a compound of formula 3c, or
b. Converting said aldehyde according to formula 2a, 2b or 2c to a corresponding amine, wherein said amine is selected from a compound of formula 4:

wherein R is selected from the group consisting of:
i.

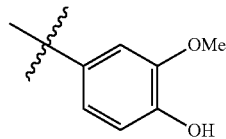

and said amine thereby being a compound of formula 4a,
ii.

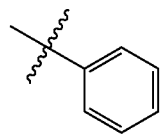 [SMILES: *c1ccccc1]

and said amine thereby being a compound of formula 4b, and
iii.

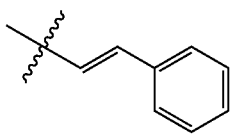 [SMILES: */C=C/c1ccccc1]

and said amine thereby being a compound of formula 4c,
wherein the conversion of aldehyde to amine is catalyzed by said enzyme cascade system.

28. The method according to claim 27, wherein the converting said alcohol to said aldehyde of formula, 2a, 2b or 2c, respectively, is carried out in the presence of Pd(o) nanoparticles.

29. The method according to claim 20, wherein:
said alcohol is vanillyl alcohol,
said aldehyde is vanillin,
said amine is vanillylamine.

30. The method according to claim 29, wherein the converting said vanillyl alcohol to said vanillin is carried out in the presence of Pd(0) nanoparticles,
wherein said enzyme cascade system further comprises one or more of D-Glucose, glucose dehydrogenase, L-alanine, NH$_3$, L-alanine dehydrogenase, and NADH.

31. The method according to claim 20, wherein said enzyme cascade system further comprises one or more of alcohol dehydrogenase (ADH) and L-ADH.

32. The method according to claim 30, wherein said Pd(0) nanoparticle is selected from the group consisting of Pd(0)-AmP-MFC and Pd(0)-CPG.

33. The method according to claim 29, wherein said vanillyl alcohol is derived from lignin.

34. The method according to claim 20, wherein said method is performed in one pot without any purification of intermediates.

35. The method according to claim 1, wherein said enzyme cascade system further comprises ATA, L-alanine as amine donor, NH3, L-alanine dehydrogenase, NADH, D-Glucose, and glucose dehydrogenase.

* * * * *